United States Patent
Hosseini et al.

(10) Patent No.: US 12,303,220 B2
(45) Date of Patent: May 20, 2025

(54) AUTONOMOUS ENDOBRONCHIAL ACCESS WITH AN EM GUIDED CATHETER

(71) Applicant: Covidien LP, Mansfield, MA (US)

(72) Inventors: Evan Arsham Hosseini, Eden Prairie, MN (US); Nathan J. Knutson, Long Lake, MN (US)

(73) Assignee: Covidien LP, Mansfield, MA (US)

(*) Notice: Subject to any disclaimer, the term of this patent is extended or adjusted under 35 U.S.C. 154(b) by 547 days.

(21) Appl. No.: 17/585,089

(22) Filed: Jan. 26, 2022

(65) Prior Publication Data

US 2023/0233270 A1     Jul. 27, 2023

(51) Int. Cl.

| A61B 1/00 | (2006.01) |
|---|---|
| A61B 1/018 | (2006.01) |
| A61B 1/05 | (2006.01) |
| A61B 1/267 | (2006.01) |
| A61B 34/30 | (2016.01) |
| A61B 34/10 | (2016.01) |
| A61B 34/20 | (2016.01) |

(52) U.S. Cl.
CPC .............. *A61B 34/30* (2016.02); *A61B 1/018* (2013.01); *A61B 1/05* (2013.01); *A61B 1/2676* (2013.01); *A61B 2034/107* (2016.02); *A61B 2034/2065* (2016.02); *A61B 2034/301* (2016.02)

(58) Field of Classification Search
CPC ......... A61B 1/018; A61B 1/05; A61B 1/2676; A61B 1/000094; A61B 1/0016; A61B 34/30; A61B 34/20; A61B 2034/107; A61B 2034/2065; A61B 2034/301; A61B 2017/00809

USPC ......................................................... 600/104
See application file for complete search history.

(56) References Cited

U.S. PATENT DOCUMENTS

| 4,202,352 A | 5/1980 | Osborn |
|---|---|---|
| 5,358,496 A | 10/1994 | Ortiz et al. |
| 6,086,586 A | 7/2000 | Hooven |
| 6,533,784 B2 | 3/2003 | Truckai et al. |
| 6,656,177 B2 | 12/2003 | Truckai et al. |
| 6,802,843 B2 | 10/2004 | Truckai et al. |

(Continued)

FOREIGN PATENT DOCUMENTS

| BR | 0013237 A | 7/2003 |
|---|---|---|
| BR | 0116004 A | 6/2004 |

(Continued)

OTHER PUBLICATIONS

Extended European Search Report issued in European Patent Application No. 23153302.7 dated Jun. 5, 2023.

*Primary Examiner* — Timothy J Neal
*Assistant Examiner* — James Edward Boice
(74) *Attorney, Agent, or Firm* — Weber Rosselli & Cannon LLP

(57) ABSTRACT

A system for performing a surgical procedure includes a controller including a memory and a processor, the memory storing instructions, which when executed by the processor cause the processor to receive an image captured by a camera, generate a segmented image by applying a first threshold value to the image captured by the camera, identify a lumen within the segmented image, determine a centroid of the lumen within the segmented image, and align a portion of a surgical device operably coupled to the controller with the centroid of the lumen.

20 Claims, 10 Drawing Sheets

(56) References Cited

U.S. PATENT DOCUMENTS

| | | |
|---|---|---|
| 6,835,336 B2 | 12/2004 | Watt |
| 6,913,579 B2 | 7/2005 | Truckai et al. |
| 7,806,891 B2 | 10/2010 | Nowlin et al. |
| 7,947,000 B2 | 5/2011 | Vargas et al. |
| 8,052,636 B2 | 11/2011 | Moll et al. |
| 8,190,238 B2 | 5/2012 | Moll et al. |
| 8,335,359 B2 | 12/2012 | Fidrich et al. |
| 8,600,551 B2 | 12/2013 | Itkowitz et al. |
| 8,706,184 B2 | 4/2014 | Mohr et al. |
| 8,827,934 B2 | 9/2014 | Chopra et al. |
| 8,914,150 B2 | 12/2014 | Moll et al. |
| 9,119,654 B2 | 9/2015 | Ramans et al. |
| 9,393,000 B2 | 7/2016 | Donhowe |
| 9,801,630 B2 | 10/2017 | Harris et al. |
| 9,839,481 B2 | 12/2017 | Blumenkranz et al. |
| 9,918,659 B2 | 3/2018 | Chopra et al. |
| 9,993,313 B2 | 6/2018 | Schuh et al. |
| 10,172,973 B2 | 1/2019 | Vendely et al. |
| 10,206,686 B2 | 2/2019 | Swayze et al. |
| 10,349,938 B2 | 7/2019 | Widenhouse et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,482,599 B2 | 11/2019 | Mintz et al. |
| 10,524,866 B2 | 1/2020 | Srinivasan et al. |
| 10,539,478 B2 | 1/2020 | Lin et al. |
| 10,543,048 B2 | 1/2020 | Noonan |
| 10,555,788 B2 | 2/2020 | Panescu et al. |
| 10,610,306 B2 | 4/2020 | Chopra |
| 10,631,949 B2 | 4/2020 | Schuh et al. |
| 10,638,953 B2 | 5/2020 | Duindam et al. |
| 10,639,108 B2 | 5/2020 | Romo et al. |
| 10,653,866 B2 | 5/2020 | Duindam et al. |
| 10,667,871 B2 | 6/2020 | Romo et al. |
| 10,667,875 B2 | 6/2020 | DeFonzo et al. |
| 10,674,970 B2 | 6/2020 | Averbuch et al. |
| 10,682,070 B2 | 6/2020 | Duindam |
| 10,682,192 B2 | 6/2020 | Fenech |
| 10,706,543 B2 | 7/2020 | Donhowe et al. |
| 10,709,506 B2 | 7/2020 | Coste-Maniere et al. |
| 10,716,637 B2 | 7/2020 | Kowshik et al. |
| 10,729,886 B2 | 8/2020 | Fenech et al. |
| 10,743,751 B2 | 8/2020 | Landey et al. |
| 10,744,303 B2 | 8/2020 | Duindam et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 10,772,485 B2 | 9/2020 | Schlesinger et al. |
| 10,779,803 B2 | 9/2020 | Prisco et al. |
| 10,779,898 B2 | 9/2020 | Hill et al. |
| 10,786,329 B2 | 9/2020 | Schuh et al. |
| 10,792,022 B2 | 10/2020 | Keast et al. |
| 10,792,464 B2 | 10/2020 | Romo et al. |
| 10,796,432 B2 | 10/2020 | Mintz et al. |
| 10,813,539 B2 | 10/2020 | Graetzel et al. |
| 10,820,947 B2 | 11/2020 | Julian |
| 10,820,954 B2 | 11/2020 | Marsot et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,842,575 B2 | 11/2020 | Panescu et al. |
| 10,842,581 B2 | 11/2020 | Bailey |
| 10,849,591 B2 | 12/2020 | Azizian et al. |
| 10,850,013 B2 | 12/2020 | Hsu et al. |
| 10,856,855 B2 | 12/2020 | Gordon |
| 10,881,280 B2 | 1/2021 | Baez, Jr. |
| 10,881,385 B2 | 1/2021 | Fenech |
| 10,885,630 B2 | 1/2021 | Li et al. |
| 2003/0013972 A1 | 1/2003 | Makin |
| 2005/0107808 A1 | 5/2005 | Evans et al. |
| 2005/0165276 A1 | 7/2005 | Belson et al. |
| 2006/0235457 A1 | 10/2006 | Belson |
| 2007/0135803 A1 | 6/2007 | Belson |
| 2010/0204545 A1 | 8/2010 | Tanaka et al. |
| 2011/0085720 A1* | 4/2011 | Averbuch ............... A61B 34/20 382/203 |
| 2013/0096385 A1 | 4/2013 | Fenech et al. |
| 2013/0303945 A1 | 11/2013 | Blumenkranz et al. |
| 2014/0035798 A1 | 2/2014 | Kawada et al. |
| 2014/0052018 A1 | 2/2014 | Hawkins |
| 2014/0235943 A1 | 8/2014 | Paris et al. |
| 2015/0148690 A1 | 5/2015 | Chopra et al. |
| 2015/0265368 A1 | 9/2015 | Chopra et al. |
| 2016/0001038 A1 | 1/2016 | Romo et al. |
| 2016/0067450 A1 | 3/2016 | Kowshik |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0256230 A1 | 9/2016 | Kowshik et al. |
| 2016/0270865 A1 | 9/2016 | Landey et al. |
| 2016/0270870 A1 | 9/2016 | Kowshik |
| 2016/0287344 A1 | 10/2016 | Donhowe et al. |
| 2016/0331358 A1 | 11/2016 | Gordon |
| 2016/0338783 A1 | 11/2016 | Romo et al. |
| 2016/0374676 A1 | 12/2016 | Flanagan et al. |
| 2017/0020628 A1 | 1/2017 | Averbuch |
| 2017/0112366 A1 | 4/2017 | Duindam et al. |
| 2017/0112576 A1 | 4/2017 | Coste-Maniere et al. |
| 2017/0112588 A1 | 4/2017 | Bissing et al. |
| 2017/0151026 A1 | 6/2017 | Panescu et al. |
| 2017/0209071 A1 | 7/2017 | Zhao et al. |
| 2017/0224338 A1 | 8/2017 | Sung |
| 2017/0238795 A1 | 8/2017 | Blumenkranz et al. |
| 2017/0258309 A1 | 9/2017 | Deyanov |
| 2017/0265952 A1 | 9/2017 | Donhowe et al. |
| 2017/0273542 A1 | 9/2017 | Au |
| 2017/0273712 A1 | 9/2017 | Carlson et al. |
| 2017/0274189 A1 | 9/2017 | Smith et al. |
| 2017/0281287 A1 | 10/2017 | Au |
| 2017/0281288 A1 | 10/2017 | Au |
| 2017/0311844 A1 | 11/2017 | Zhao et al. |
| 2017/0319165 A1 | 11/2017 | Averbuch |
| 2017/0325896 A1 | 11/2017 | Donhowe et al. |
| 2018/0001058 A1 | 1/2018 | Schlesinger |
| 2018/0056040 A1 | 3/2018 | Fenech et al. |
| 2018/0064904 A1 | 3/2018 | Vargas et al. |
| 2018/0070935 A1 | 3/2018 | Fenech |
| 2018/0078318 A1 | 3/2018 | Barbagli et al. |
| 2018/0153621 A1 | 6/2018 | Duindam et al. |
| 2018/0214011 A1 | 8/2018 | Graetzel et al. |
| 2018/0214138 A9 | 8/2018 | Prisco et al. |
| 2018/0221038 A1 | 8/2018 | Noonan et al. |
| 2018/0221039 A1 | 8/2018 | Shah |
| 2018/0235565 A1 | 8/2018 | Azizian et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0280660 A1 | 10/2018 | Landey et al. |
| 2018/0296281 A1 | 10/2018 | Yeung et al. |
| 2018/0325419 A1 | 11/2018 | Zhao et al. |
| 2018/0325499 A1 | 11/2018 | Landey et al. |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0076143 A1 | 3/2019 | Smith |
| 2019/0110839 A1 | 4/2019 | Rafii-Tari et al. |
| 2019/0110843 A1 | 4/2019 | Ummalaneni |
| 2019/0133702 A1 | 5/2019 | Fenech et al. |
| 2019/0167366 A1 | 6/2019 | Ummalaneni et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192143 A1 | 6/2019 | Shelton, IV et al. |
| 2019/0192234 A1 | 6/2019 | Gadda et al. |
| 2019/0192819 A1 | 6/2019 | Duindam et al. |
| 2019/0200984 A1 | 7/2019 | Shelton, IV et al. |

(56) References Cited

U.S. PATENT DOCUMENTS

| | | |
|---|---|---|
| 2019/0209016 A1 | 7/2019 | Herzlinger et al. |
| 2019/0209043 A1 | 7/2019 | Zhao et al. |
| 2019/0216447 A1 | 7/2019 | Bailey et al. |
| 2019/0216548 A1 | 7/2019 | Ummalaneni |
| 2019/0223693 A1 | 7/2019 | Vargas |
| 2019/0223759 A1 | 7/2019 | Page et al. |
| 2019/0231449 A1 | 8/2019 | Diolaiti et al. |
| 2019/0239723 A1 | 8/2019 | Duindam et al. |
| 2019/0239724 A1 | 8/2019 | Averbuch et al. |
| 2019/0239831 A1 | 8/2019 | Chopra |
| 2019/0246876 A1 | 8/2019 | Schaning |
| 2019/0246882 A1 | 8/2019 | Graetzel et al. |
| 2019/0247128 A1 | 8/2019 | Inouye et al. |
| 2019/0250050 A1 | 8/2019 | Sanborn et al. |
| 2019/0254649 A1 | 8/2019 | Walters et al. |
| 2019/0262086 A1 | 8/2019 | Connolly et al. |
| 2019/0269468 A1 | 9/2019 | Hsu et al. |
| 2019/0269470 A1 | 9/2019 | Barbagli et al. |
| 2019/0269885 A1 | 9/2019 | Bailey et al. |
| 2019/0272634 A1 | 9/2019 | Li et al. |
| 2019/0290109 A1 | 9/2019 | Agrawal et al. |
| 2019/0290375 A1 | 9/2019 | Dearden et al. |
| 2019/0298160 A1 | 10/2019 | Ummalaneni et al. |
| 2019/0298451 A1 | 10/2019 | Wong et al. |
| 2019/0298460 A1 | 10/2019 | Al-Jadda et al. |
| 2019/0298465 A1 | 10/2019 | Chin et al. |
| 2019/0320878 A1 | 10/2019 | Duindam et al. |
| 2019/0320937 A1 | 10/2019 | Duindam et al. |
| 2019/0328213 A1 | 10/2019 | Landey et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0350660 A1 | 11/2019 | Moll et al. |
| 2019/0350662 A1 | 11/2019 | Huang et al. |
| 2019/0365199 A1 | 12/2019 | Zhao et al. |
| 2019/0365201 A1 | 12/2019 | Noonan et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0000533 A1 | 1/2020 | Schuh et al. |
| 2020/0000537 A1 | 1/2020 | Marsot et al. |
| 2020/0008655 A1 | 1/2020 | Schlesinger et al. |
| 2020/0008678 A1 | 1/2020 | Barbagli et al. |
| 2020/0008827 A1 | 1/2020 | Dearden et al. |
| 2020/0008874 A1 | 1/2020 | Barbagli et al. |
| 2020/0022762 A1 | 1/2020 | Cassell et al. |
| 2020/0022767 A1 | 1/2020 | Hill et al. |
| 2020/0029948 A1 | 1/2020 | Wong et al. |
| 2020/0030044 A1 | 1/2020 | Wang et al. |
| 2020/0030461 A1 | 1/2020 | Sorger |
| 2020/0030575 A1 | 1/2020 | Bogusky et al. |
| 2020/0038123 A1 | 2/2020 | Graetzel et al. |
| 2020/0038750 A1 | 2/2020 | Kojima |
| 2020/0039086 A1 | 2/2020 | Meyer et al. |
| 2020/0043207 A1 | 2/2020 | Lo et al. |
| 2020/0046431 A1 | 2/2020 | Soper et al. |
| 2020/0046434 A1 | 2/2020 | Graetzel et al. |
| 2020/0046436 A1 | 2/2020 | Tzeisler et al. |
| 2020/0054399 A1 | 2/2020 | Duindam et al. |
| 2020/0060516 A1 | 2/2020 | Baez, Jr. |
| 2020/0060771 A1 | 2/2020 | Lo et al. |
| 2020/0069192 A1 | 3/2020 | Sanborn et al. |
| 2020/0069384 A1 | 3/2020 | Fenech et al. |
| 2020/0077870 A1 | 3/2020 | Dicarlo et al. |
| 2020/0077991 A1 | 3/2020 | Gordon et al. |
| 2020/0078095 A1 | 3/2020 | Chopra et al. |
| 2020/0078096 A1 | 3/2020 | Barbagli et al. |
| 2020/0078103 A1 | 3/2020 | Duindam et al. |
| 2020/0078104 A1 | 3/2020 | Bailey et al. |
| 2020/0085514 A1 | 3/2020 | Blumenkranz |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100776 A1 | 4/2020 | Blumenkranz et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0107894 A1 | 4/2020 | Wallace et al. |
| 2020/0107899 A1 | 4/2020 | Carlson et al. |
| 2020/0109124 A1 | 4/2020 | Pomper et al. |
| 2020/0121170 A1 | 4/2020 | Gordon et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0146757 A1 | 5/2020 | Fenech et al. |
| 2020/0155116 A1 | 5/2020 | Donhowe et al. |
| 2020/0163581 A1 | 5/2020 | Kowshik et al. |
| 2020/0163726 A1 | 5/2020 | Tanner et al. |
| 2020/0170623 A1 | 6/2020 | Averbuch |
| 2020/0170720 A1 | 6/2020 | Ummalaneni |
| 2020/0171660 A1 | 6/2020 | Ho et al. |
| 2020/0179058 A1 | 6/2020 | Barbagli et al. |
| 2020/0188038 A1 | 6/2020 | Donhowe et al. |
| 2020/0197112 A1 | 6/2020 | Chin et al. |
| 2020/0198147 A1 | 6/2020 | Fredrickson et al. |
| 2020/0205903 A1 | 7/2020 | Srinivasan et al. |
| 2020/0205904 A1 | 7/2020 | Chopra |
| 2020/0205908 A1 | 7/2020 | Julian et al. |
| 2020/0206472 A1 | 7/2020 | Ma et al. |
| 2020/0214664 A1 | 7/2020 | Zhao et al. |
| 2020/0217733 A1 | 7/2020 | Lin et al. |
| 2020/0222134 A1 | 7/2020 | Schuh et al. |
| 2020/0222666 A1 | 7/2020 | Chan et al. |
| 2020/0229679 A1 | 7/2020 | Zhao et al. |
| 2020/0237458 A1 | 7/2020 | DeFonzo et al. |
| 2020/0242767 A1 | 7/2020 | Zhao et al. |
| 2020/0253670 A1 | 8/2020 | Doisneau et al. |
| 2020/0254223 A1 | 8/2020 | Duindam et al. |
| 2020/0261172 A1 | 8/2020 | Romo et al. |
| 2020/0261175 A1 | 8/2020 | Fenech |
| 2020/0268240 A1 | 8/2020 | Blumenkranz et al. |
| 2020/0268459 A1 | 8/2020 | Noonan |
| 2020/0268463 A1 | 8/2020 | Au |
| 2020/0275860 A1 | 9/2020 | Duindam |
| 2020/0275984 A1 | 9/2020 | Brisson et al. |
| 2020/0281787 A1 | 9/2020 | Ruiz |
| 2020/0289023 A1 | 9/2020 | Duindam et al. |
| 2020/0297437 A1 | 9/2020 | Schuh et al. |
| 2020/0297442 A1 | 9/2020 | Adebar et al. |
| 2020/0305983 A1 | 10/2020 | Yampolsky et al. |
| 2020/0305989 A1 | 10/2020 | Schuh et al. |
| 2020/0315554 A1 | 10/2020 | Averbuch et al. |
| 2020/0323593 A1 | 10/2020 | Coste-Maniere et al. |
| 2020/0330167 A1 | 10/2020 | Romo et al. |
| 2020/0330795 A1 | 10/2020 | Sawant et al. |
| 2020/0345436 A1 | 11/2020 | Kowshik et al. |
| 2020/0352420 A1 | 11/2020 | Graetzel et al. |
| 2020/0352427 A1 | 11/2020 | Deyanov |
| 2020/0352675 A1 | 11/2020 | Averbuch |
| 2020/0364865 A1 | 11/2020 | Donhowe et al. |
| 2020/0367719 A1 | 11/2020 | Au |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383750 A1 | 12/2020 | Kemp et al. |
| 2020/0391010 A1 | 12/2020 | Fenech et al. |
| 2020/0405317 A1 | 12/2020 | Wallace |
| 2020/0405411 A1 | 12/2020 | Draper et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2021/0121051 A1* | 4/2021 | Altshuler ............ A61B 1/0057 |
| 2022/0286602 A1* | 9/2022 | Ben Hassen ............ G06T 7/60 |
| 2023/0363836 A1* | 11/2023 | Pandya ............ A61B 34/30 |

(56) References Cited

U.S. PATENT DOCUMENTS

FOREIGN PATENT DOCUMENTS

| | | |
|---|---|---|
| CZ | 486540 B1 | 9/2016 |
| CZ | 2486540 | 9/2016 |
| CZ | 2709512 | 8/2017 |
| CZ | 3060157 | 12/2019 |
| CZ | 2884879 B1 | 1/2020 |
| EP | 3326551 A1 | 5/2018 |
| EP | 3367915 A4 | 7/2019 |
| EP | 3413830 A4 | 9/2019 |
| EP | 3562423 A1 | 11/2019 |
| EP | 3552653 A3 | 12/2019 |
| EP | 3576598 A1 | 12/2019 |
| EP | 3576599 A1 | 12/2019 |
| EP | 3478161 A4 | 2/2020 |
| EP | 3641686 A2 | 4/2020 |
| EP | 3644820 A1 | 5/2020 |
| EP | 3644885 A1 | 5/2020 |
| EP | 3644886 A1 | 5/2020 |
| EP | 3645100 A1 | 5/2020 |
| EP | 3654870 A2 | 5/2020 |
| EP | 3668582 A2 | 6/2020 |
| EP | 3576599 A4 | 11/2020 |
| MX | PA03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |

\* cited by examiner

AUTONOMOUS ENDOBRONCHIAL ACCESS WITH AN EM GUIDED CATHETER

BACKGROUND

Technical Field

The present disclosure relates to the field of visualizing the navigation of medical devices, such as biopsy or ablation tools, relative to targets, and in particular, navigating medical devices to a target.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient. To enable the endoscopic approach endoscopic navigation systems have been developed that use previously acquired MRI data or CT image data to generate a three-dimensional (3D) rendering, model, or volume of the particular body part such as the lungs.

The resulting volume generated from the MRI scan or CT scan is then utilized to create a navigation plan to facilitate the advancement of the endoscope (or other suitable medical device) within the patient anatomy to an area of interest. A locating or tracking system, such as an electromagnetic (EM) tracking system, may be utilized in conjunction with, for example, CT data, to facilitate guidance of the endoscope to the area of interest.

However, manually navigating the endoscope through the luminal network or utilizing robotic controls to remotely navigate the endoscope through the luminal network can be complex and time consuming. Further, navigating the endoscope through the luminal network takes considerable skill to ensure no damage is done to the surrounding tissue and that the endoscope is navigated to the correct location.

SUMMARY

In accordance with the present disclosure, a system for performing a surgical procedure includes a controller operably coupled to a camera, the controller including a memory and a processor, the memory storing instructions, which when executed by the processor, cause the processor to receive an image captured by the camera, generate a segmented image by applying a first threshold value to the image captured by the camera, identify a lumen within the segmented image, determine a centroid of the lumen within the segmented image, and align a portion of a surgical device operably coupled to the controller with the centroid of the lumen.

In aspects, the segmented image may be generated using dynamic binary thresholding.

In other aspects, the system may include a surgical device, wherein the camera is disposed on a distal portion of the surgical device, wherein the surgical device is navigable within a portion of the patient's anatomy.

In certain aspects, the system may include a robotic surgical system operably coupled to the surgical device.

In other aspects, the instructions, when executed by the processor, may cause the robotic surgical system to align the surgical device with the centroid of the lumen.

In aspects, the instruction, when executed by the processor, may cause the processor to generate a pathway to a target tissue.

In certain aspects, the instructions, when executed by the processor, may cause the processor to identify a lumen within the image corresponding to the pathway to the target tissue.

In other aspects, the instruction, when executed by the processor, may cause the robotic surgical system to advance the surgical device within the lumen within the image corresponding to the pathway to the target tissue.

In aspects, the instructions, when executed by the processor, may cause the processor to determine a centroid of the lumen within the segmented image in real-time.

In other aspects, the instruction, when executed by the processor, may cause the robotic surgical system to maintain alignment of the distal portion of the surgical device with the centroid of the lumen within the segmented image as the surgical device is advanced within the lumen.

In accordance with another aspect of the present disclosure, a method of performing a surgical procedure includes receiving an image of a patient's anatomy from a camera operably coupled to a surgical device, generating a segmented image by applying a first threshold value to the image, identifying a lumen within the segmented image, determining a centroid of the lumen within the segmented image, and aligning the surgical deice with the centroid of the lumen.

In aspects, generating the segmented image may include applying dynamic binary thresholding utilizing the first threshold value to generate the segmented image.

In other aspects, the method may include applying a second threshold value to the segmented image.

In certain aspects, the method may include generating a binary image from the segmented image.

In other aspects, the method may include generating a pathway through a patient's anatomy to a target tissue.

In aspects, the method may include advancing the surgical device through the patient's anatomy following the centroid of the lumen and the pathway through the patient's anatomy.

In accordance with another aspect of the present disclosure, a system for performing a surgical procedure includes a robotic surgical system including an endoscope including a camera, the camera disposed on a portion of the endoscope, and a drive mechanism operably coupled to the endoscope, a controller operably coupled to the robotic surgical system, the controller including a memory and a processor, the memory storing instructions, which when executed by the processor cause the processor to receive an image captured by the camera, generate a segmented image by applying a first threshold value to the image captured by the camera, identify a centroid of the lumen, and cause the drive mechanism to align a distal end portion of the endoscope with the centroid of the lumen.

In aspects, the instructions, when executed by the processor, may cause the processor to generate a pathway to a target tissue located within a patient's anatomy.

In other aspects, the instructions, when executed by the processor, may cause the processor to cause the drive mechanism to advance the distal end portion of the endoscope along the pathway.

In certain aspects, the instructions, when executed by the processor, may cause the processor to continuously update the centroid of the lumen as the endoscope is advanced along the pathway.

BRIEF DESCRIPTION OF THE DRAWINGS

Various aspects and embodiments of the disclosure are described hereinbelow with references to the drawings, wherein.

DETAILED DESCRIPTION

Figure 1:
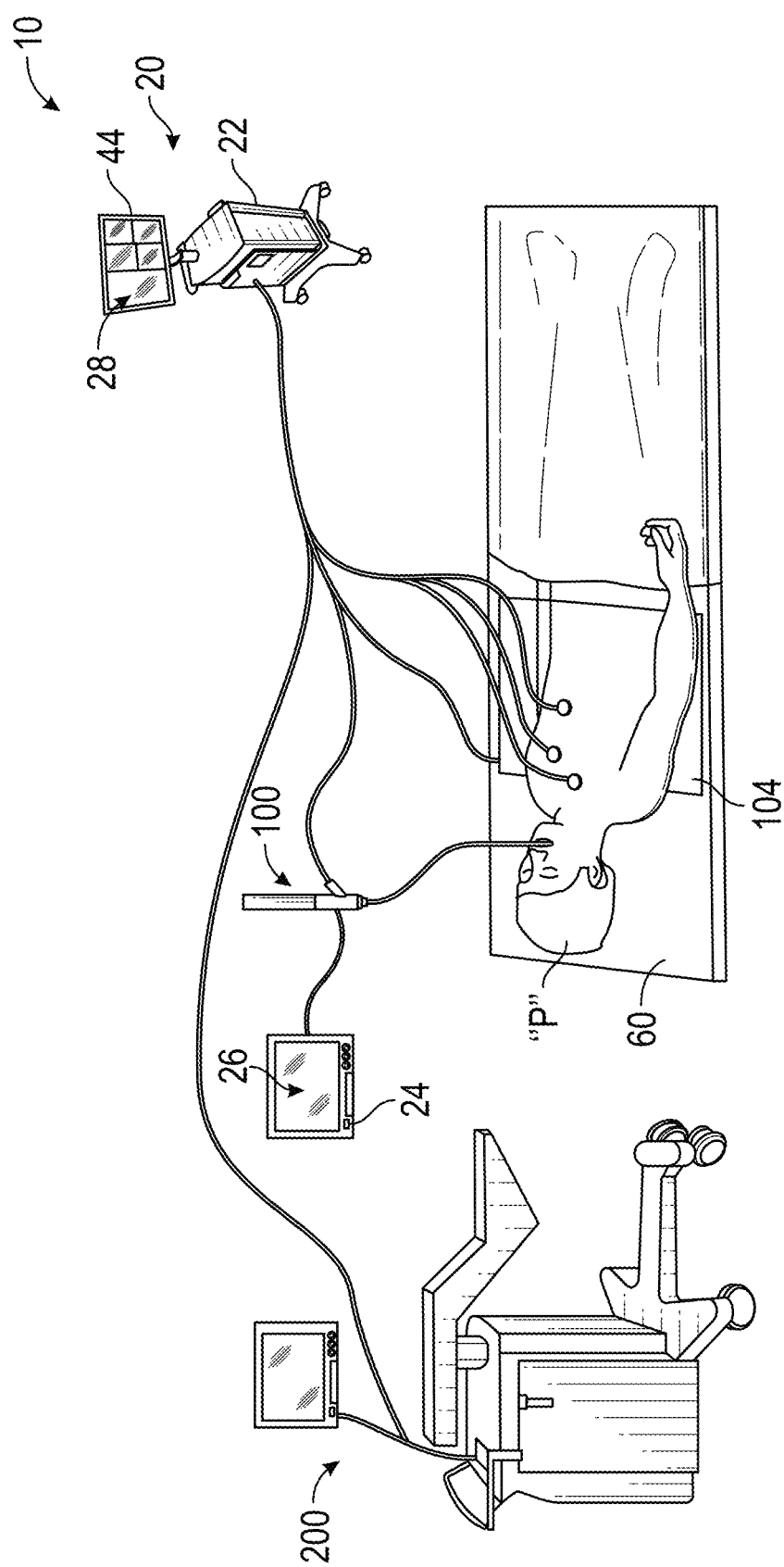
FIG. 1 is a schematic view of a surgical system provided in accordance with the present disclosure.

The present disclosure is directed to a surgical system having a controller or workstation operably coupled to an endoscope, which in turn, is operably coupled to a robotic surgical system. The controller is configured to generate a 3D model of a patient's lungs and generate a pathway through the luminal network of the patient's lung to reach target tissue. The controller is operably coupled to an electromagnetic navigation system, which is configured to identify a location of a distal end portion of the endoscope within the liminal network of the patient's lungs using an electromagnetic sensor disposed within the endoscope and an electromagnetic field generator disposed proximate the patient.

The endoscope includes a camera, which in embodiments can be a miniature CMOS camera, which captures images of the patient's anatomy as the endoscope is navigated through the luminal network of the patient's lungs. The software associated with the controller analyzes the images captured by the camera disposed on the endoscope, which in embodiments, may be continuous throughout navigation of the endoscope to the target tissue. Initially, the software converts white light images captured by the camera to grayscale images, which in turn, are segmented into two portions by comparing the pixels within the grayscale image to a first threshold value. In embodiments, the software application segments the image using dynamic binary thresholding, which determines a mean value of pixels in each of the two segmented portions. After initial segmentation, the software application averages the mean values of the pixels of each of the two segmented portions and calculates an updated threshold value. If the updated threshold value is below a specified limit, the segmented image is re-segmented using the updated threshold value and the average of the mean values of the pixels is once again calculated and compared to the specified limit. If the updated threshold value is above a specified limit, the software generates a binary image, illustrating tissue walls in one color and lumens within the image as another. In one non-limiting embodiment, the tissue walls are illustrated as black whereas the lumens are illustrated as white. Although generally described as updating a threshold value and re-segmenting the image, it is envisioned that the software application may utilize Otsu's method, wherein automatic image thresholding is performed by automatically identifying a single intensity threshold that separates pixels identified in the image into two classes, foreground and background. It is envisioned that the software application may assign labels, such as a translucent color, to each lumen identified in the image, which can be overlaid on the live image captured by the camera disposed on the endoscope.

The software application compares the image captured by the endoscope to pre-procedure images, and in conjunction with the electromagnetic sensor, determines a location at which the image was captured within the luminal network of the patient's lungs. With the location known, the pathway to the target tissue may be overlaid on the live image and the software may select the appropriate lumen within the image to traverse to maintain course on the pathway and reach the target tissue.

The surgical system of the present disclosure enables automated navigation of the endoscope within the luminal network of the patient's lungs to the target issue by calculating a centroid of the lumens from the segmented images. In this manner, each lumen identified within the images includes a shape. Using the binary image, the software application is configured to calculate a centroid of the particular shape of each lumen. With the centroid of the lumen known, the software application is configured to instruct the robotic surgical system to manipulate or otherwise articulate the distal end portion of the endoscope to be aligned with the centroid of the lumen associated with the pathway to the target tissue.

Using this information, the surgical system continually analyzes the images captured by the camera disposed on the endoscope to maintain alignment of the distal end portion of the endoscope with the centroid of the lumen and avoid impacting or otherwise touching the tissue wall of the lumen. Further, monitoring the location of the endoscope within the luminal network of the patient's lungs enables the robotic surgical system to automatically manipulate and navigate the endoscope proximate the target tissue for treatment. As can be appreciated, the surgical system may perform spot checks or otherwise check that the real-time location of the endoscope is registered with the 3D model and pathway to correct any discrepancies and maintain course to the target tissue. In embodiments, a clinician may manually override automatic navigation to correct errors and reposition the endoscope to the correct location.

Although generally described with reference to the lung, it is contemplated that the systems and methods described herein may be used with any structure within the patient's body, such as the liver, kidney, prostate, gynecological, amongst others.

Turning now to the drawings, FIG. 1 illustrates a surgical system provided in accordance with the present disclosure and generally identified by reference numeral 10. As will be described in further detail hereinbelow, the surgical system 10 is generally configured to identify target tissue, register real-time images captured by a surgical instrument to a generated 3-Dimensional (3D) model, and navigate the surgical instrument to the target tissue.

The surgical system includes an endoscope 100, a controller or workstation 20 operably coupled to the endoscope 100, and a robotic surgical system 200 operably coupled to the controller 20 and operably coupled to the endoscope 100. The patient "P" is shown lying on an operating table 60 with the endoscope 100 inserted through the patient's mouth and into the patient's airways, although it is contemplated that the endoscope 100 may be inserted into any suitable body cavity of the patient, depending upon the procedure being performed.

Figure 2:
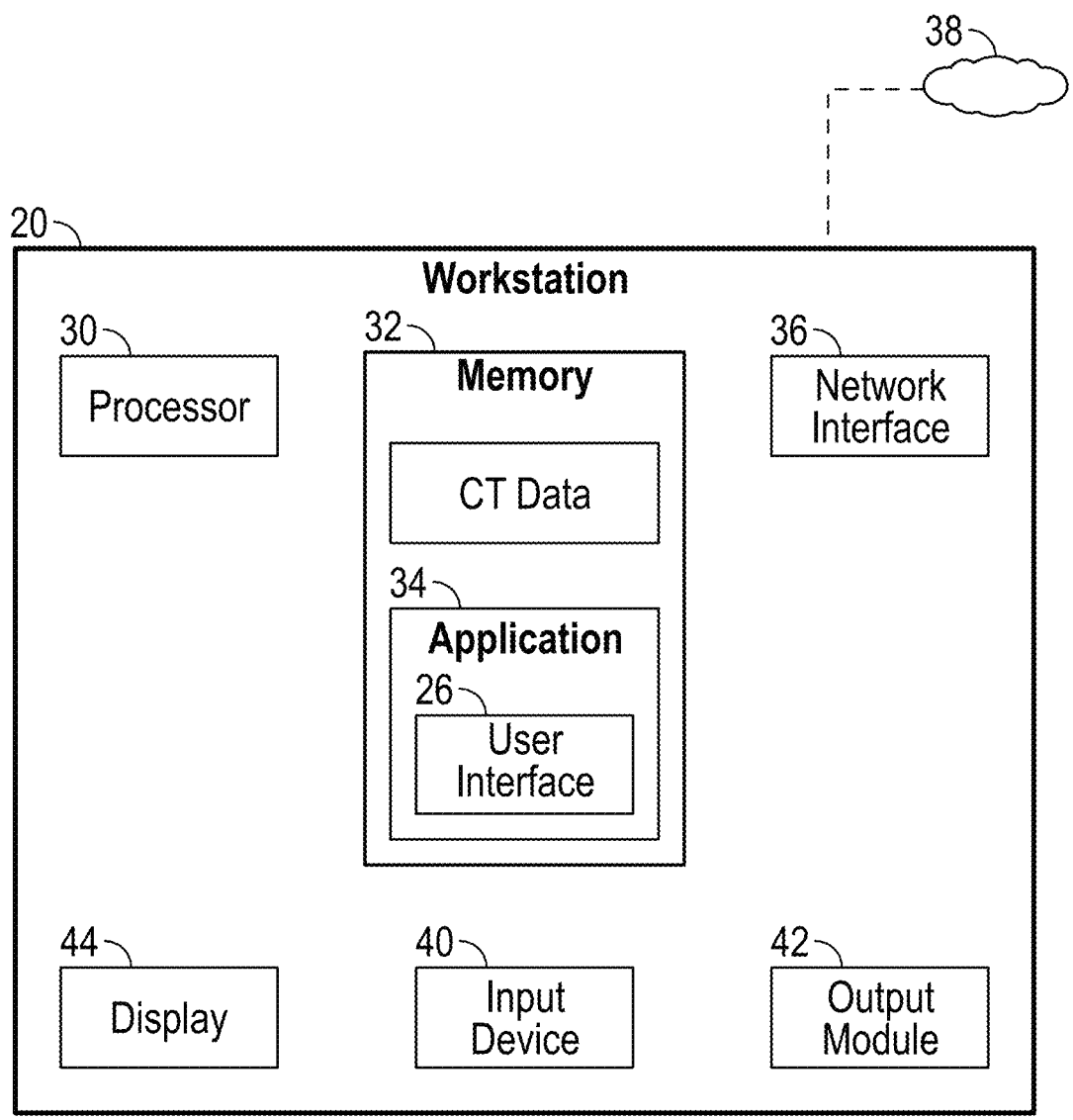
FIG. 2 is a schematic view of a controller of the surgical system of FIG. 1.

Continuing with FIG. 1 and with additional reference to FIG. 2, the controller 20 includes a computer 22 and a display 24 that is configured to display one or more user interfaces 26 and/or 28. The controller 20 may be a desktop computer or a tower configuration with the display 24 or may be a laptop computer or other computing device. The controller 20 includes a processor 30 which executes software stored in a memory 32. The memory 32 may store video or other imaging data captured by the endoscope 100 or pre-procedure images from, for example, a computer-tomography (CT) scan, Positron Emission Tomography (PET), Magnetic Resonance Imaging (MRI), Cone-beam CT, amongst others. In addition, the memory 32 may store one or more applications 34 to be executed on the processor 30. Though not explicitly illustrated, the display 24 may be incorporated into a head mounted display such as an augmented reality (AR) headset such as the HoloLens offered by Microsoft Corp.

A network interface 36 enables the controller 20 to communicate with a variety of other devices and systems via the Internet. The network interface 36 may connect the controller 20 to the Internet via a wired or wireless connection. Additionally, or alternatively, the communication may be via an ad-hoc Bluetooth® or wireless network enabling communication with a wide-area network (WAN) and/or a local area network (LAN). The network interface 36 may connect to the Internet via one or more gateways, routers, and network address translation (NAT) devices. The network interface 36 may communicate with a cloud storage system 38, in which further image data and videos may be stored. The cloud storage system 38 may be remote from or on the premises of the hospital such as in a control or hospital information technology room. An input module 40 receives inputs from an input device such as a keyboard, a mouse, voice commands, amongst others. An output module 42 connects the processor 30 and the memory 32 to a variety of output devices such as the display 24. In embodiments, the controller 20 may include its own display 44, which may be a touchscreen display.

In embodiments, the endoscope 100 includes a location sensor, such as an electromagnetic (EM) sensor 102 (FIG. 3) which receives electromagnetic signals from an electromagnetic field generator 104 (FIG. 1) which generates one or more electromagnetic fields. In one non-limiting embodiment, the EM field generator 104 generates three or more electromagnetic fields. It is envisioned that the EM sensor 102 may be a single coil sensor that enables the system 10 to identify the position of the endoscope within the EM field generated by the EM field generator 104, although it is contemplated that the EM sensor 102 may be any suitable sensor and may be a sensor capable of enabling the system 10 to identify the position, orientation, and/or pose of the endoscope 100 within the EM field.

With continued reference to FIG. 2, one of the applications 34 stored in the memory 32 and executed by the processor 30 may determine the position of the EM sensor 102 in the EM field generated by the electromagnetic field generator 104. The determination of the position of the endoscope 100 and one or more cameras disposed thereon enables one method in which the images captured by the endoscope may be registered to a generated 3D model of the patient's anatomy, as will be described in further detail hereinbelow. Although generally described as being an EM sensor, it is contemplated that other position sensors may be utilized, such as an ultrasound sensor, flex sensors, fiber Bragg grating (FBG), robotic position detections sensors, amongst others.

In a planning or pre-procedure phase, the software stored in the memory 32 and executed by the processor 30 utilizes pre-procedure CT image data, either stored in the memory 32 or retrieved via the network interface 36, for generating and viewing a 3D model of the patient's anatomy, enabling the identification of target tissue on the 3D model (automatically, semi-automatically, or manually), and in embodiments, allowing for the selection of a pathway through the patient's anatomy to the target tissue. One example of such an application is the ILOGIC® planning and navigation suites currently marketed by Medtronic. The 3D model may be displayed on the display 24 or another suitable display (not shown) associated with the controller 20, or in any other suitable fashion. Using the controller 20, various views of the 3D model may be provided and/or the 3D model may be manipulated to facilitate identification of target tissue on the 3D model and/or selection of a suitable pathway to the target tissue.

In embodiments, the software stored in the memory 32 may identify and segment out a targeted critical structure within the 3D model. It is envisioned that the segmentation process may be performed automatically, manually, or a combination of both. The segmentation process isolates the targeted critical structure from the surrounding tissue in the 3D model and identifies its position within the 3D model. As can be appreciated, this position can be updated depending upon the view selected on the display 24 such that the view of the segmented targeted critical structure may approximate a view captured by the endoscope 100, as will be described in further detail hereinbelow.

Figure 3:
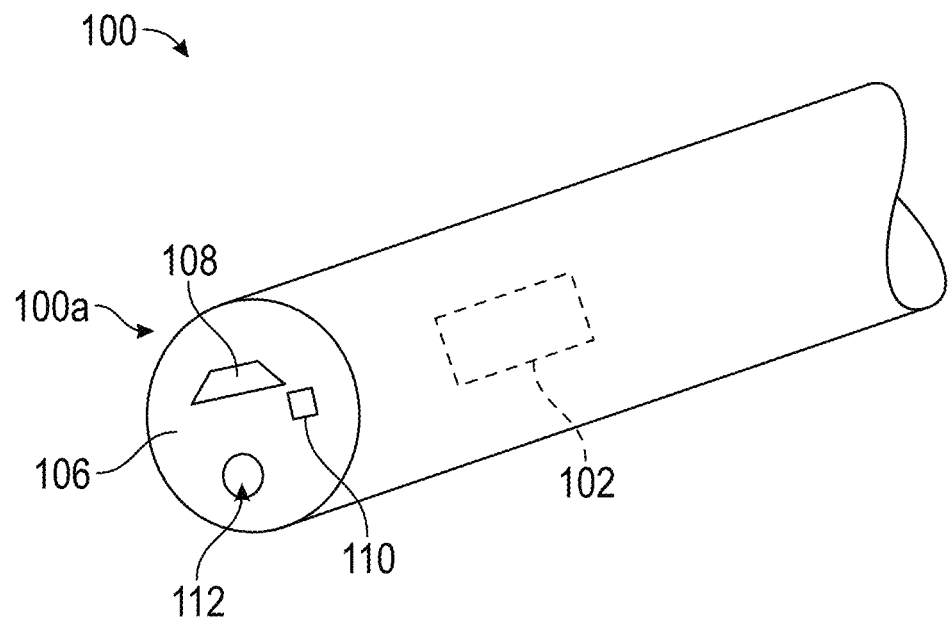
FIG. 3 is a perspective view of a distal end portion of an endoscope of the surgical system of FIG. 1.
Figure 4:
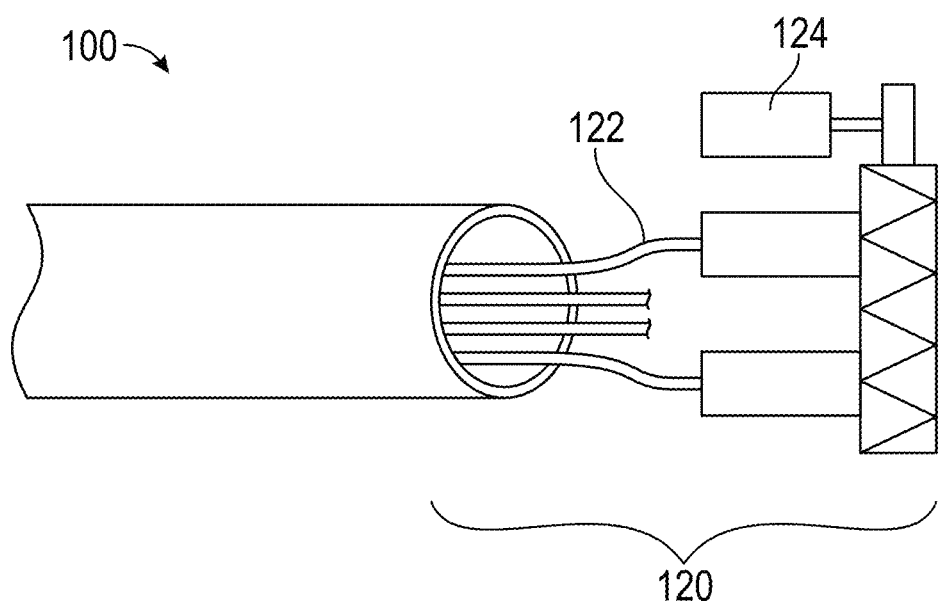
FIG. 4 is an exploded view of a drive mechanism of the endoscope of FIG. 3.

Turning to FIGS. 3-4, the endoscope 100 is illustrated and includes a distal surface 106 having a camera 108 disposed thereon. Although generally illustrated as having one camera 108, it is contemplated that the endoscope 100 may include any number of cameras disposed on the distal surface 106 or any other suitable location thereon (e.g., sidewall, etc.). It is envisioned that the camera 108 is a complementary metal-oxide-semiconductor (CMOS) camera, and in embodiments, may be a mini-CMOS camera. As can be appreciated, the camera 108 captures images of the patient's anatomy from a perspective of looking out from the distal surface 106. Although generally identified as being a CMOS camera, it is envisioned that the camera 108 may be any suitable camera, such as charge-coupled device (CCD), complementary metal-oxide-semiconductor (CMOS), N-type metal-oxide-semiconductor (NMOS), and in embodiments, may be a white light camera, infrared (IR) camera, amongst others, depending upon the design needs of the system 10.

In embodiments, the endoscope 100 may include one or more light sources 110 disposed on the distal surface 106 or any other suitable location (e.g., side surface, protuberance, etc.). The light source 110 may be or may include a light emitting diode (LED), an optical fiber connected to a light source that is located external to the patient, amongst others, and may emit white, IR, or near infrared (NIR) light. In this manner, the camera 108 may be a white light camera, IR camera, or NIR camera, a camera that is capable of capturing white light and NIR light, amongst others. In one non-limiting embodiment, the camera 108 is a white light mini-CMOS camera.

The endoscope 100 includes one or more working channels 112 defined therethrough and extending through the distal surface 106. The working channel 112 is configured to receive a tool (not shown), locatable guide (LG), amongst others to enable a clinician to navigate to, or treat, target tissue. It is contemplated that the tool may be any suitable tool utilized during an endoscopic surgical procedure, and in embodiments, may be a fixed tool.

With reference to FIG. 4 the endoscope 100 includes a drive mechanism 120 disposed within an interior portion thereof that is operably coupled to a proximal portion of the endoscope 100. The drive mechanism 120 effectuates manipulation or articulation of a distal portion 100a of the endoscope 100 in four degrees of freedom (e.g., left, right, up, down), which is controlled by two push-pull wires, although it is contemplated that the drive mechanism 120 may include any suitable number of wires to effectuate movement and/or articulation of the distal portion 100a of the endoscope 100 in greater or fewer degrees of freedom without departing from the scope of the present disclosure. It is envisioned that the drive mechanism 120 may be cable actuated using artificial tendons or pull wires 122 (e.g., metallic, non-metallic, composite, etc.) or may be a nitinol wire mechanism. In embodiments, the drive mechanism 120 may include motors 124 or other suitable devices capable of effectuating movement of the pull wires 122. In this manner, the motors 124 are disposed within the endoscope 100 such that rotation of the motors 124 effectuates a corresponding articulation of the distal portion 100a of the endoscope 100.

Figure 5:
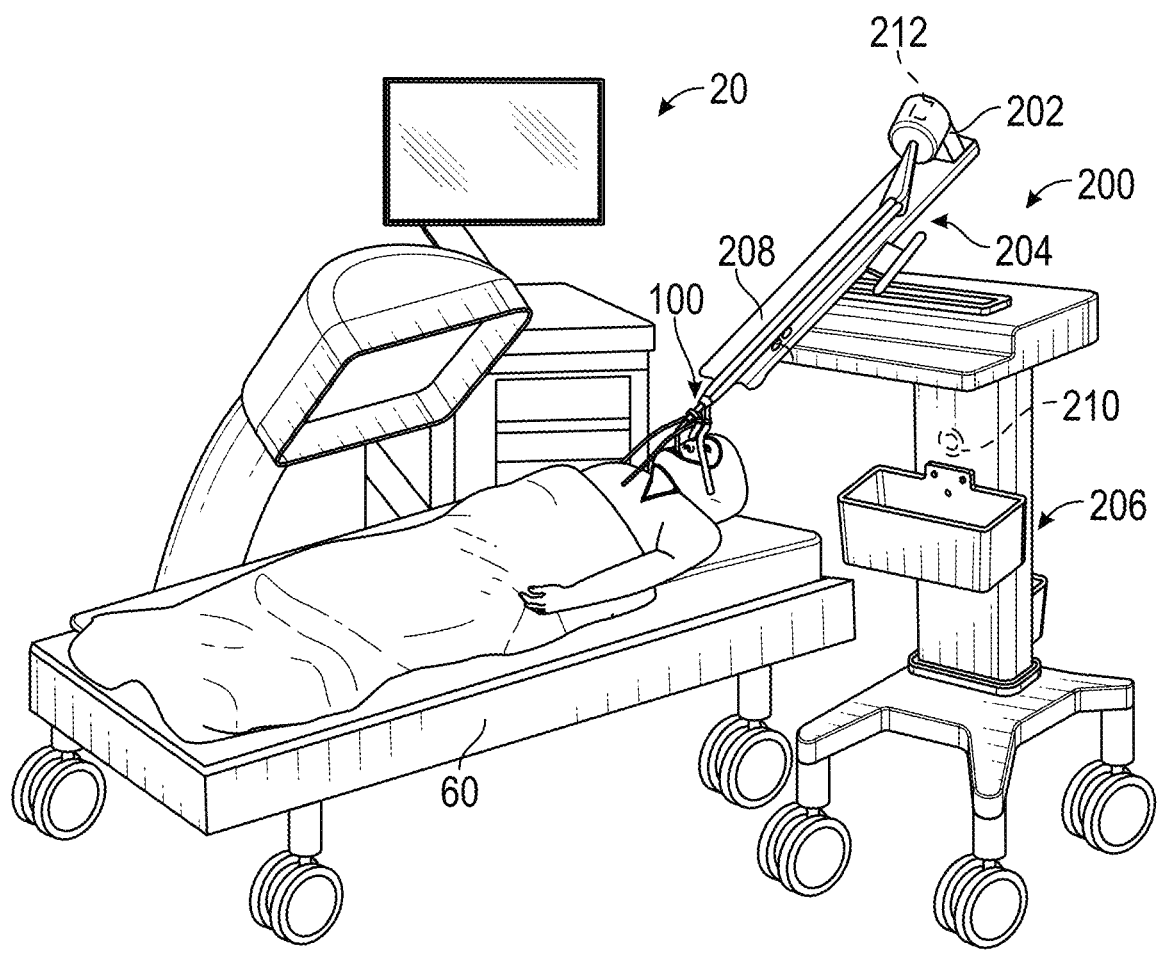
FIG. 5 is a perspective view of a robotic surgical system of the surgical system of FIG. 1.

Turning to FIG. 5, the system 10 includes a robotic surgical system 200 that is operably coupled to the endoscope 100. The robotic surgical system 200 includes a drive mechanism 202 including a robotic arm 204 operably coupled to a base or cart 206. The robotic arm 204 includes a cradle 208 that is configured to receive a portion of the endoscope 100 thereon. The endoscope 100 is coupled to the cradle 208 using any suitable means (e.g., straps, mechanical fasteners, couplings, amongst others).

It is envisioned that the robotic surgical system 200 may communicate with the endoscope 100 via electrical connection (e.g., contacts, plugs, etc.) or may be in wireless communication with the endoscope 100 to control or otherwise effectuate movement of the motors 124 and receive images captured by the camera 108. In this manner, it is contemplated that the robotic surgical system 200 may include a wireless communication system 210 operably coupled thereto such that the endoscope 100 may wirelessly communicate with the robotic surgical system 200 and/or the controller 20 via Wi-Fi, Bluetooth®, amongst others. As can be appreciated, the robotic surgical system 200 may omit the electrical contacts altogether and may communicate with the endoscope 100 wirelessly or may utilize both electrical contacts and wireless communication. The wireless communication system 210 is substantially similar to the wireless network interface 28 of the controller 20, and therefore, the wireless communication system 210 will not be described in detail herein in the interest of brevity. In embodiments, the robotic surgical system 200 and the controller 20 may be one in the same or may be widely distributed over multiple locations within the operating room. It is contemplated that the controller 20 may be disposed in a separate location and the display 12 may be an overhead monitor disposed within the operating room.

Although generally described as having the motors 124 disposed within the endoscope 100, it is contemplated that the endoscope 100 may not include motors 124 disposed therein. In this manner, the drive mechanism 120 disposed within the endoscope 100 may interface with motors 124 disposed within the cradle 208 of the robotic surgical system 200. In embodiments, the endoscope 100 may include a motor or motors 124 for controlling articulation of the distal end portion 100a of the endoscope in one plane (e.g., left/null, right/null, etc.) and the drive mechanism 202 of the robotic surgical system 200 may include at least one motor 212 to effectuate the second axis of rotation and for axial motion. In this manner, the motor 124 of the endoscope 100 and the motors 212 of the robotic surgical system 200 cooperate to effectuate four-way articulation of the distal end portion 100a of the endoscope 100 and effectuate rotation of the endoscope 100. As can be appreciated, by removing the motors 124 from the endoscope 100, the endoscope 100 becomes increasingly cheaper to manufacture and may be a disposable unit. In embodiments, the endoscope 100 may be integrated into the robotic surgical system 200 (e.g., one piece) and may not be a separate component.

With reference to FIGS. 6-11, the software stored in the memory 32 communicates with the camera 108 to capture images in real-time of the patient's anatomy as the endoscope 100 is navigated through the luminal network of the patient. The software includes two tiers or processes; the first being the image processing tier, and the second being the navigation tier.

Figure 7:
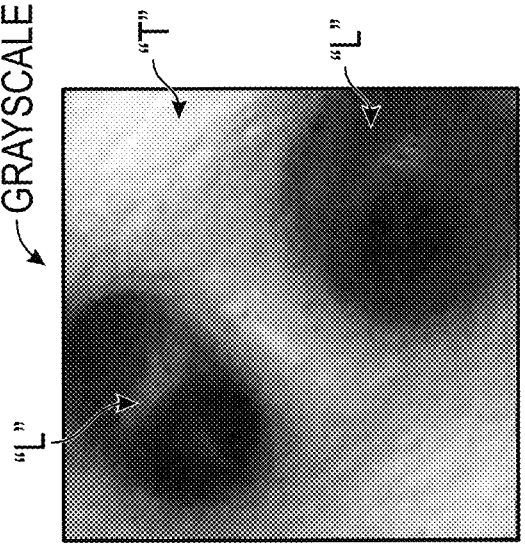
FIG. 7 is a depiction of the graphical user interface of FIG. 6 illustrating a grayscale version of the color image of FIG. 6.

The first tier of the software application segments the images captured by the camera 108 using dynamic binary thresholding. In this manner, if the images captured by the camera 108 are captured in color (e.g., white light) (FIG. 6), the software converts the color image into a grayscale image (FIG. 7). At this point, the software segments the image using dynamic binary thresholding to divide the image into two portions, a background portion and a foreground portion. The background portion includes pixel values that are less than or equal to a selected threshold and the foreground portion includes pixel values that are greater than the selected threshold. This process is repeated by averaging mean values of the two portions of the image and calculating a new threshold by averaging the two means until the difference between the previous threshold value and the new threshold value are below a selected limit. Although generally described as updating a threshold value and re-segmenting the image, it is envisioned that the software application may utilize Otsu's method, wherein automatic image thresholding is performed by automatically identifying a single intensity threshold that separates pixels identified in the image into two classes, foreground and background. In this manner, the software application dynamically computes a threshold based upon the distribution of pixel intensities within the image to group the pixels into two classes, foreground and background. As such, a single threshold is utilized and the segmentation process is performed a single time for each image frame, reducing the amount of time, and processing power, to perform the segmentation process.

Figure 9:
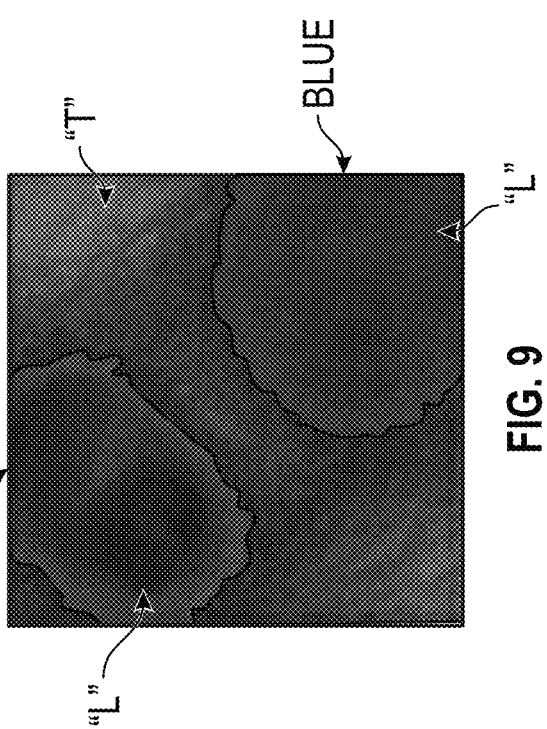
FIG. 9 is a depiction of the graphical user interface of FIG. 6 illustrating labels overlaid on the color image of FIG. 6.
Figure 6:
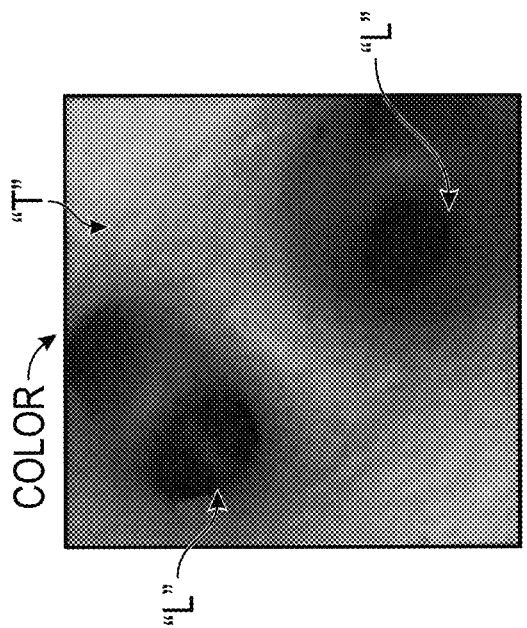
FIG. 6 is a depiction of a graphical user interface of the surgical system of FIG. 1 illustrating a color image.
Figure 8:
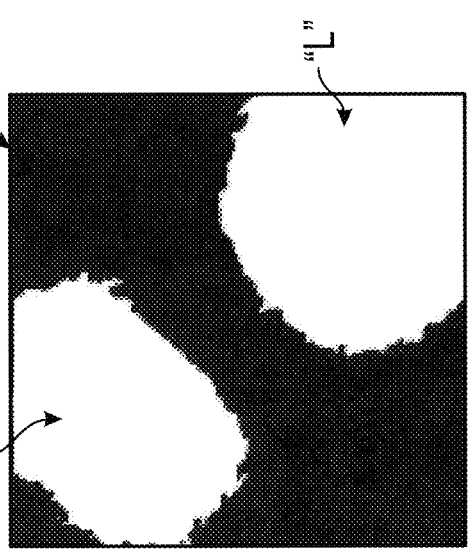
FIG. 8 is a depiction of the graphical user interface of FIG. 6 illustrating a binary version of the grayscale image of FIG. 7.

The result of the dynamic binary thresholding process is an image in black and white, illustrating the foreground in white and the background in black, or vice versa (e.g., a binary image). In one non-limiting embodiment, the first tier of the software identifies the tissue walls "T" in black and the lumen "L" of the luminal network present in the image in white (FIG. 8). With the lumens "L" within the image identified, the software overlays the black and white image over the grayscale image with the black portion removed and the white portions illustrated as being a translucent color, such as yellow, red, amongst others to create a labeled image (FIG. 9). In one non-limiting embodiment, each lumen "L" identified by the software is illustrated as a different color (e.g., the first lumen "L" is identified by red, the second lumen is identified by blue, etc.).

Figure 10:
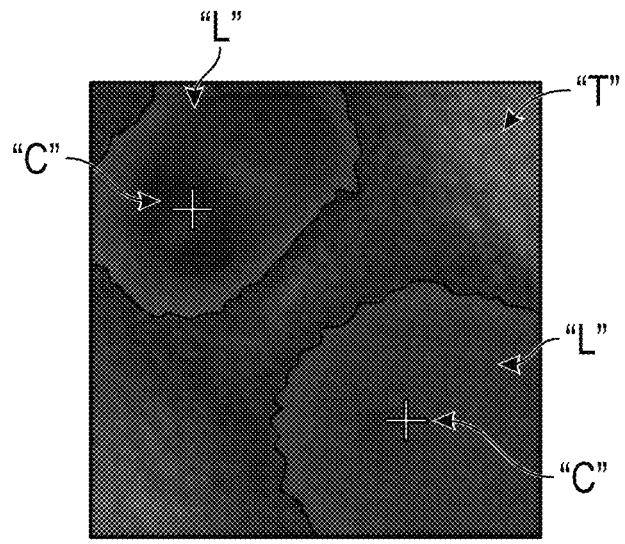
FIG. 10 is a depiction of the graphical user interface of FIG. 6 illustrating a marker corresponding to a centroid of each lumen identified in the image of FIG. 9.

With reference to FIG. 10, the second tier of the software application stored on the memory 32 utilizes the labeled image to identify a centroid or center portion of the identified lumens. As can be appreciated, the use of dynamic binary thresholding to identify each lumen within an image creates a shape from which the centroid "C" can be calculated. Using the calculated centroid, the software application controls or manipulates the distal end portion 100a of the endoscope 100 to aim or otherwise align the distal end portion 100a of the endoscope 100 with the centroid "C" of the lumen "L". As can be appreciated, the software application continuously analyzes each image of the images captured by the camera in real time to ensure the distal end portion 100a of the endoscope 100 is aligned with the centroid of the lumen to inhibit or otherwise minimize the chances of the distal end portion 100a of the endoscope 100 from contacting a sidewall of the lumen.

Figure 11:
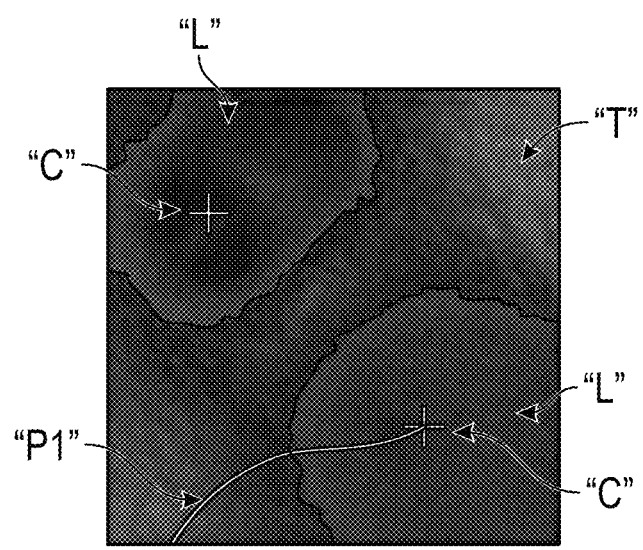
FIG. 11 is a depiction of the graphical user interface of FIG. 6 illustrating a pathway to target tissue overlaid on the image of FIG. 10.

In embodiments, the second tier of the software application overlays the pathway "P1" generated and selected by the clinician to the selected area of interest or target tissue (FIG. 11). In this manner, the software application utilizes the EM sensor 102 to identify the location of the distal end portion 100a of the endoscope within the airways of the patient's lungs and compares the images captured by the camera 108 to the pre-procedure images to register or otherwise ensure that the distal end portion 100a of the endoscope 100 is in the proper location within the airways of the patient's lungs. It is envisioned that the position of the endoscope 100 within the patient's lungs may be registered to the generated 3D model automatically via software or manually. In embodiments, the software application continuously checks the position of the endoscope within the patient's lungs as compared to the location indicated within the 3D model via the EM sensor 102 and/or the images captured by the camera 108. It is envisioned that the software application can automatically adjust the position of the endoscope 100 indicated within the 3D model due to tidal breathing or the respiration rate of the patient using any suitable means.

In operation, the endoscope is advanced, retracted, and manipulated within the patient's lungs automatically via the software application and the robotic surgical system 200. In this manner, the software application continuously communicates with the camera 108 and identifies the position of the EM sensor 102 within the electromagnetic field generated by the EM field generator 104. Utilizing the pathway selected by the clinician in conjunction with pre-procedure images stored on the memory 32, the software application identifies the position of the distal end portion 100a of the endoscope 100 within the patient's lungs. At this point, the first tier of the software application identifies each lumen of the lungs visible within the filed of view of the camera 108 and determines a centroid of each lumen via the methods described hereinabove. Using the identified centroid of each lumen, the software application instructs the robotic surgical system 200 to advance the endoscope 100, retract the endoscope 100, manipulate the distal end portion 100a of the endoscope 100 up, down, left, or right, and/or rotate the endoscope to maintain the position of the distal end portion 100a of the endoscope substantially aligned with the centroid of the lumen.

When the distal end portion 100a of the endoscope 100 encounters a bifurcation within the patient's luminal network, the software application identifies the lumen through which the endoscope 100 must travel to remain on the selected pathway to the target tissue. At this point, the software application instructs the robotic surgical system 200 to manipulate the distal end portion 100a of the endoscope 100 to align the distal end portion 100a with the centroid of the appropriate lumen and further advances the endoscope within the luminal network of the patient's lungs until the distal end portion 100a of the endoscope 100 is proximate the target tissue. It is envisioned that the software application may periodically or continuously confirm the location of the distal end portion 100a of the endoscope 100 within the patient's luminal network as compared to the location indicated on the 3D model of the patient's lung and update the indicated location on the 3D model as necessary to ensure that the endoscope is following the correct path through the luminal network. Once the distal end portion 100a of the endoscope 100 has been navigated proximate the target tissue, one or more tools or other surgical devices may be advanced through the one or more working channels 112 to treat the target tissue.

Figure 12A:
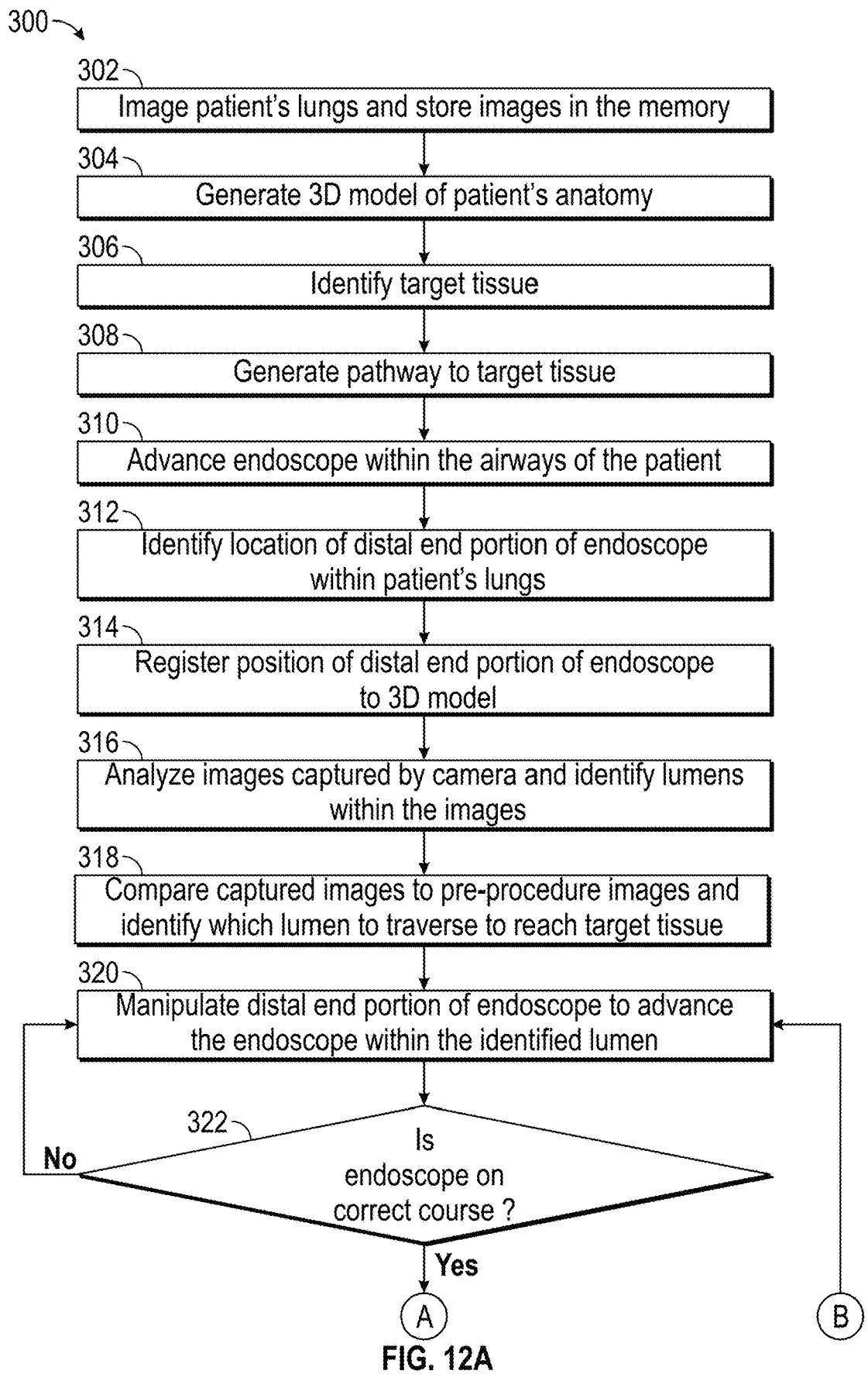
FIG. 12A is a flow diagram of a method of navigating a surgical instrument to target tissue in accordance with the present disclosure.
Figure 12B:
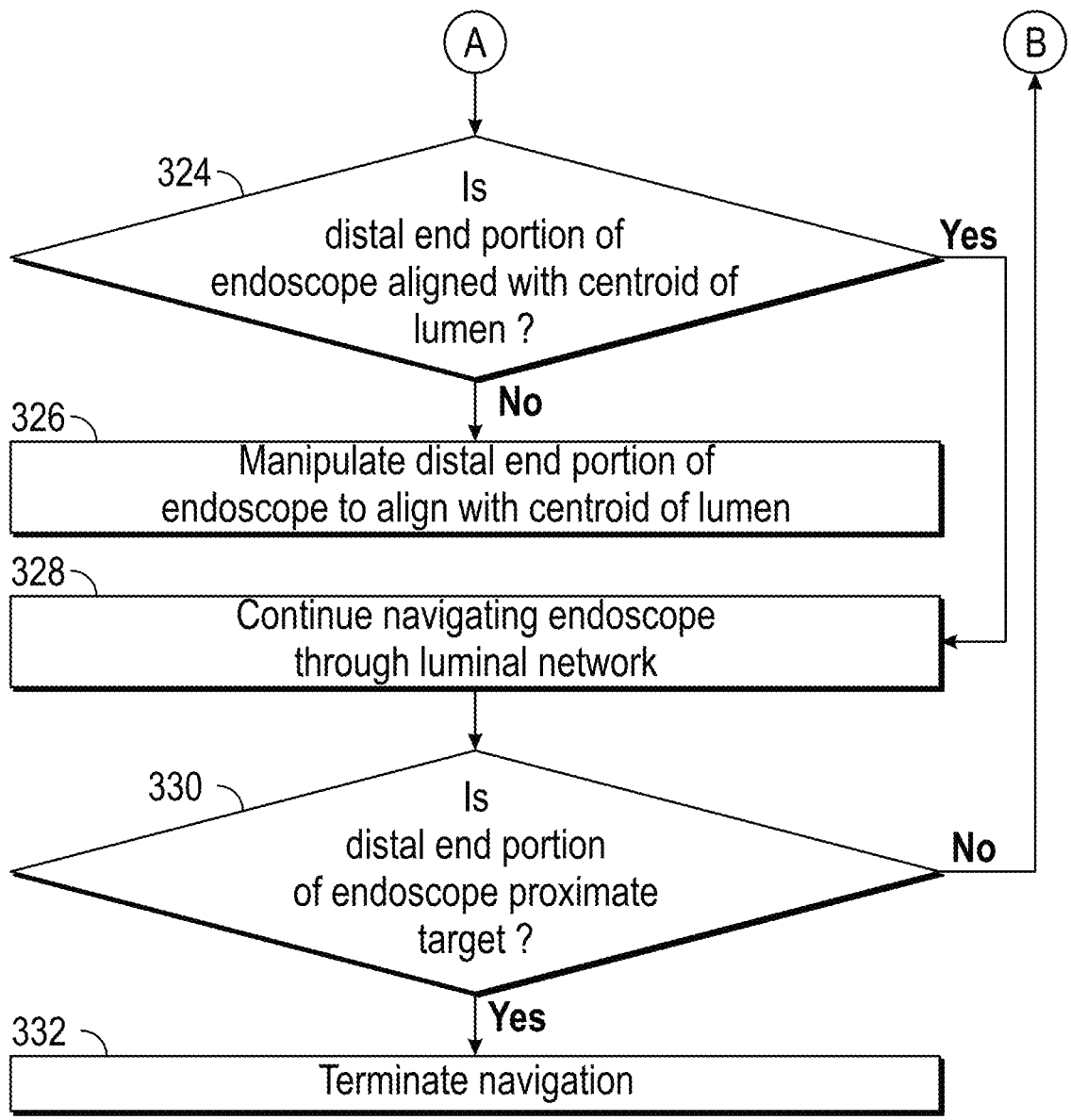
FIG. 12B is a continuation of the flow diagram of FIG. 12A.

Turning to FIGS. 12A and 12B, a method of navigating an endoscope through a luminal network of a patient's lungs to a target tissue is described and generally identified by reference numeral 300. Initially, in step 302, the patient's lungs are imaged using any suitable imaging modality (e.g., CT, MRI, amongst others) and the images are stored in the memory 32 associated with the controller 20. In step 304, the images stored on the memory 32 are utilized to generate and viewing a 3D model of the patient's anatomy, and thereafter, target tissue is identified in step 306. With the target tissue identified, a pathway to the target tissue through the luminal network of the patient's lungs is generated in step 308.

Once the desired pathway to the target tissue is selected, the surgical procedure is initiated in step 310 by advancing the distal end portion 100a of the endoscope 100 within the airways of the patient's lungs. With the distal end portion 100a of the endoscope 100 disposed within the airways of the patient's lungs, the location of the distal end portion 100a of the endoscope 100 is identified in step 312 using the camera 108 and the EM sensor 102 of the endoscope and the identified position of the distal end portion 100a of the endoscope is registered to the 3D model and the selected pathway to the target tissue in step 314. After registration, the software application analyzes images captured by the camera 108 and identifies lumens of luminal network of the patient's lungs visible in the field of view of the camera 108 and determines a centroid of the lumens in step 316. In step 318, with the lumens identified within the images captured by the camera 108, the software application compares the images captured by the camera 108 to the pre-procedure images and identifies a lumen through which the endoscope 100 must traverse to maintain its course on the selected pathway to the target tissue. After selecting the appropriate lumen, the software application instructs the robotic surgical system 200 to manipulate or otherwise control the distal end portion 100a of the endoscope 100 to advance within the selected lumen in step 320.

In step 322, the software application checks the location of the distal end portion 100a of the endoscope 100 within the patient's luminal network and determines if the endoscope 100 is on the pathway or is off course. If the endoscope 100 is not on the desired pathway, the method returns to step 320 to cause the robotic surgical system to retract the endoscope and/or manipulate the endoscope to the appropriate location within the patient's luminal network to place the distal end portion 100a of the endoscope 100 back on the desired pathway. If the endoscope 100 is on the desired pathway, in step 324, the software application monitors the images captured by the camera 108 and determines if the distal end portion 100a of the endoscope 100 is substantially aligned with the centroid of the lumen through which the distal end portion 100a of the endoscope 100 is traversing. If the software application determines that the distal end portion 100a of the endoscope 100 is not substantially aligned with the centroid of the lumen, the software application instructs the robotic surgical system 200 to manipulate or otherwise control the distal end portion 100a of the endoscope to re-align with the centroid of the lumen in step 326. If the software application determines that the distal end portion 100a is substantially aligned with the centroid of the lumen, in step 328, the software application continues navigating the endoscope 100 through the luminal network along the selected pathway.

In step 330, the software application determines if the distal end portion 100a of the endoscope is located proximate the target tissue, and if so, terminates navigation of the endoscope in step 332. If the software application determines that the distal end portion 100a of the endoscope 100 is not located proximate the target tissue, the software application returns to step 320 to continue navigating the endoscope through the luminal network of the patient's lungs along the selected pathway until the software application determines that the distal end portion 100a of the endoscope 100 is located proximate the target tissue.

Figure 13A:
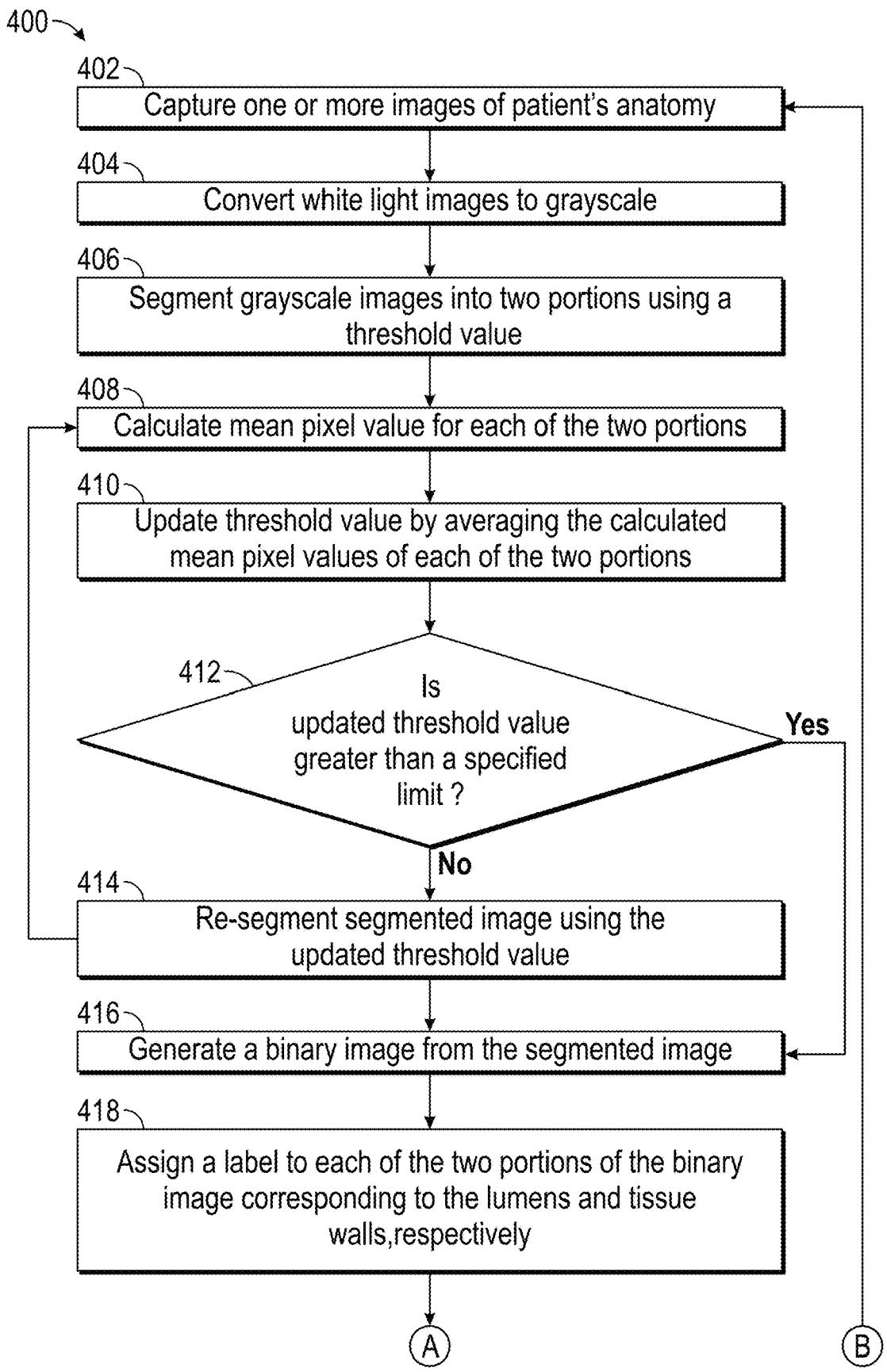
FIG. 13A is a flow diagram of a method of identifying a centroid of a lumen of a luminal network in accordance with the present disclosure.
Figure 13B:
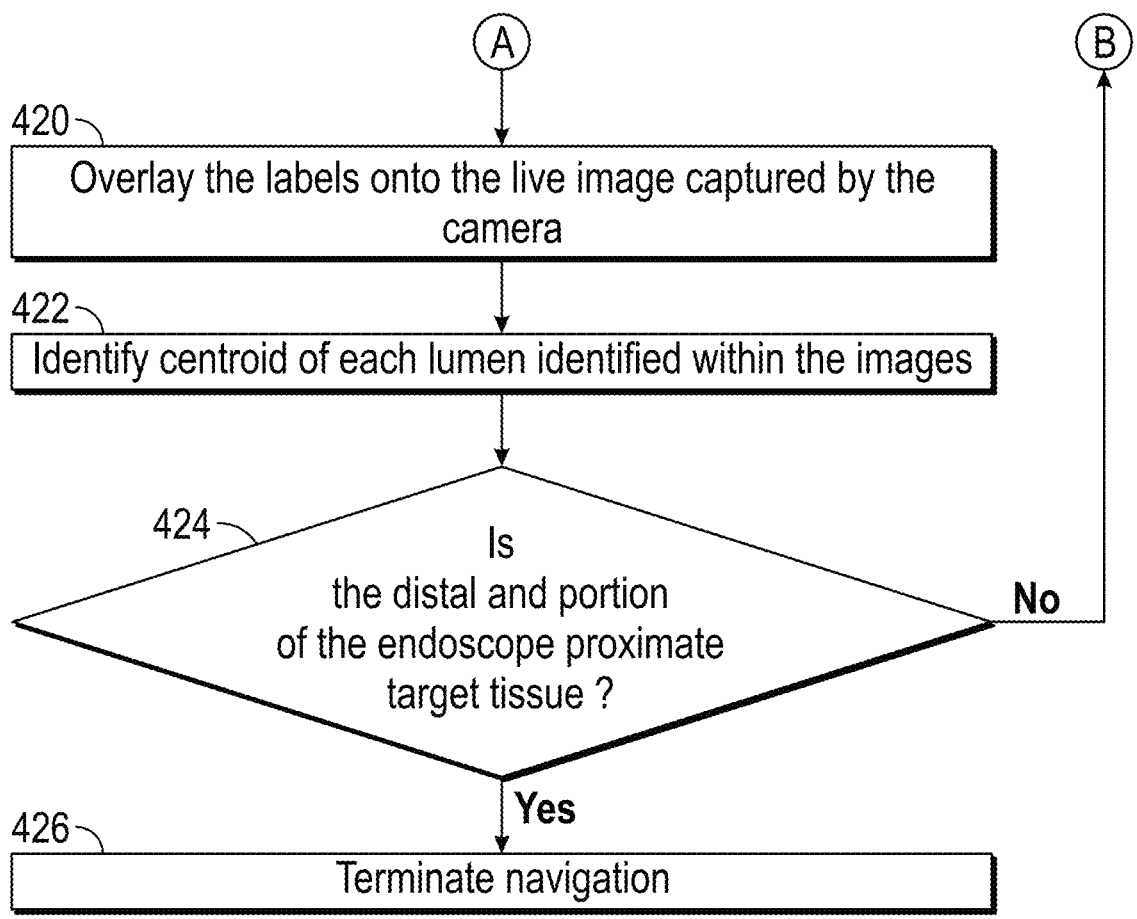
FIG. 13B is a continuation of the flow diagram of FIG. 13A.

With reference to FIGS. 13A and 13B, a method of identifying a centroid of a lumen of a luminal network of a patient's lungs is illustrated and generally identified by reference numeral 400. Initially, in step 402 one or more images of the patient's anatomy proximate the distal end portion 100a are captured by the camera 108. If the images captured by the camera 108 are in color, the color images are converted to grayscale images in step 404. In step 406, with the images converted to grayscale, a grayscale image of the one or more captured images is segmented using dynamic binary thresholding to divide the image into two portions; a first portion including pixel values that are greater than a first threshold and a second portion including pixel values that are equal to or less than the first threshold. After the initial segmentation, in step 408, the mean value of the pixel values of each of the two portions of the image is calculated, and in step 410, an updated threshold value is calculated by averaging the calculated mean values of the first and second portions. In step 412, the updated threshold value is compared to a specified limit, and if the updated threshold value is below the specified limit, the image is segmented a second time by again dividing the image into two portions utilizing the updated threshold value in step 414, at which point the process returns to step 410. As can be appreciated, steps 406-414 are repeated as many times as necessary until the updated threshold value is determined to be greater than the specified limit, at which point, in step 416, a binary image (e.g., black and white image) is generated illustrating the two portions in contrasting colors. In embodiments, as described in further detail hereinabove, the process may segment the image a single time by dynamically identifying a threshold value based upon the distribution of pixel intensities identified in the image. In this manner, the process performs step 406 and skips to step 416, as the re-segmentation process is unnecessary.

In step 418, the two portions of the binary image are assigned labels corresponding to the lumens and the tissue walls within the image, and in step 420, the labels are overlaid on the color or live image captured by the camera 108. In step 422, the centroid of the identified lumens is calculated utilizing the shape of the lumen or lumens identified in the binary image. Although generally described as being calculated after assigning labels, it is envisioned that the centroid of the lumen may be calculated at any time after the binary image is generated. Once the centroid of the lumen has been calculated, the process returns to step 402 and is continuously repeated as the endoscope 100 is advanced within the luminal network of the patient's lungs and new images are captured until it is determined, in step 424, that the endoscope 100 is located proximate the target tissue. If it is determined that the endoscope 100 is located proximate target tissue, navigation of the endoscope 100 within the patient's lungs terminates in step 426.

Although described generally hereinabove, it is envisioned that the memory 32 may include any non-transitory computer-readable storage media for storing data and/or software including instructions that are executable by the processor 30 and which control the operation of the controller 20 and, in some embodiments, may also control the operation of the endoscope 100. In an embodiment, memory 32 may include one or more storage devices such as solid-state storage devices, e.g., flash memory chips. Alternatively, or in addition to the one or more solid-state storage devices, the memory 32 may include one or more mass storage devices connected to the processor 30 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 30. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the controller 20.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A system for performing a surgical procedure, comprising:
a controller operably coupled to a camera, the controller including a memory and a processor, the memory storing instructions, which when executed by the processor cause the processor to:
receive a color image captured by the camera;
convert the color image to a grayscale image;
generate a segmented image by applying a first threshold value to the grayscale image captured by the camera;
identify a lumen within the segmented image;
determine a centroid of the lumen within the segmented image;
overlay the segmented image on the grayscale image, wherein the identified lumen of the segmented image is depicted as a translucent color; and
articulate a portion of a surgical device operably coupled to the controller to align the portion of the surgical device with the centroid of the lumen.

2. The system according to claim 1, wherein the segmented image is generated using dynamic binary thresholding.

3. The system according to claim 1, further including a surgical device, wherein the camera is disposed on a distal portion of the surgical device, wherein the surgical device is navigable within a portion of a patient's anatomy.

4. The system according to claim 3, further including a robotic surgical system operably coupled to the surgical device.

5. The system according to claim 4, wherein the instructions, when executed by the processor, cause the robotic surgical system to align the surgical device with the centroid of the identified lumen.

6. The system according to claim 5, wherein the instructions, when executed by the processor, cause the processor to generate a pathway to a target tissue.

7. The system according to claim 6, wherein the instructions, when executed by the processor, cause the processor to identify a lumen within the image corresponding to the pathway to the target tissue.

8. The system according to claim 7, wherein the instruction, when executed by the processor, cause the robotic surgical system to advance the surgical device within the lumen within the image corresponding to the pathway to the target tissue.

9. The system according to claim 8, wherein the instructions, when executed by the processor, cause the processor to determine a centroid of the identified lumen within the segmented image in real-time.

10. The system according to claim 9, wherein the instructions, when executed by the processor, cause the robotic surgical system to maintain alignment of the distal portion of the surgical device with the centroid of the identified lumen within the segmented image as the surgical device is advanced within the identified lumen.

11. A method of performing a surgical procedure, comprising:
receiving a color image of a patient's anatomy from a camera operably coupled to a surgical device;
convert the color image to a grayscale image;
generating a segmented image by applying a first threshold value to the grayscale image;
identifying a lumen within the segmented image;
determining a centroid of the lumen within the segmented image;
overlay the segmented image on the grayscale image, wherein the identified lumen of the segmented image is depicted as a translucent color; and
articulating the surgical device to align the surgical device with the centroid of the lumen.

12. The method according to claim 11, wherein generating the segmented image includes applying dynamic binary thresholding utilizing the first threshold value to generate the segmented image.

13. The method according to claim 12, further comprising applying a second threshold value to the segmented image.

14. The method according to claim 12, further comprising generating a binary image from the segmented image.

15. The method according to claim 11, further comprising generating a pathway through a patient's anatomy to a target tissue.

16. The method according to claim 15, further comprising advancing the surgical device through the patient's anatomy following the centroid of the identified lumen and the pathway through the patient's anatomy.

17. A system for performing a surgical procedure, comprising: a robotic surgical system, comprising:
an endoscope including a camera, the camera disposed on a portion of the endoscope; and
a drive mechanism operably coupled to the endoscope; and
a controller operably coupled to the robotic surgical system, the controller including a memory and a processor, the memory storing instructions, which when executed by the processor cause the processor to:
receive a color image captured by the camera;
convert the color image to a grayscale image;
generate a segmented image by applying a first threshold value to the grayscale image captured by the camera;
identify a lumen within the segmented image;
determine a centroid of the lumen;
overlay the segmented image on the grayscale image, wherein the identified lumen of the segmented image is depicted as a translucent color; and
cause the drive mechanism to articulate a distal end portion of the endoscope to align the distal portion of the endoscope with the centroid of the lumen.

18. The system according to claim 17, wherein the instructions, when executed by the processor, cause the processor to generate a pathway to a target tissue located within a patient's anatomy.

19. The system according to claim 18, wherein the instructions, when executed by the processor, cause the processor to cause the drive mechanism to advance the distal end portion of the endoscope along the pathway.

20. The system according to claim 19, wherein the instructions, when executed by the processor, cause the processor to continuously update the centroid of the identified lumen as the endoscope is advanced along the pathway.

\* \* \* \* \*